United States Patent [19]

Sturgeon

[11] Patent Number: 4,465,076
[45] Date of Patent: Aug. 14, 1984

[54] SELF-APPLYING ACCESSORY FOR BLOOD PRESSURE CUFF

[76] Inventor: Harvey H. Sturgeon, Rte. 0, New Florence, Mo. 63363

[21] Appl. No.: 395,738

[22] Filed: Jul. 6, 1982

[51] Int. Cl.³ .............................................. A61B 5/02
[52] U.S. Cl. .................................... 128/686; 128/677; 128/327
[58] Field of Search ............................... 128/677–686, 128/327

[56] References Cited

U.S. PATENT DOCUMENTS

| | | | |
|---|---|---|---|
| 2,320,179 | 5/1943 | Gray | 128/686 |
| 3,587,584 | 6/1971 | Keller | 128/327 |
| 3,633,567 | 1/1972 | Sarnoff | 128/686 |
| 3,906,937 | 9/1975 | Aronson | 128/686 |
| 3,929,129 | 12/1975 | Archambault | 128/677 |
| 3,968,788 | 7/1976 | Hopkins | 128/686 |
| 4,007,734 | 2/1977 | Peters | 128/686 |
| 4,033,337 | 7/1977 | Raczkowski | 128/686 |
| 4,354,503 | 10/1982 | Golden | 128/686 |

Primary Examiner—Lee S. Cohen
Assistant Examiner—Angela D. Sykes
Attorney, Agent, or Firm—Kalish & Gilster

[57] ABSTRACT

A sphygmomanometer comprising a cuff for embracing the arm of a patient having a pair of sections in normally endwise relationship with cooperating fasteners for retaining the cuff in operative position. An accessory in the nature of a cord is mounted upon one section for cooperating with same to form an arm-receiving loop and to thereupon constitute an expedient for tightening such loop to reliably position the related section and to retain same against shifting while the other section is being directed about the arm in order to bring the cooperating fastening elements into operative mating relationship so that the cuff is firmly positioned for instrument operation without the services or assistance of another individual.

6 Claims, 10 Drawing Figures

SELF-APPLYING ACCESSORY FOR BLOOD PRESSURE CUFF

BACKGROUND AND SUMMARY OF THE INVENTION

This invention relates in general to sphygmomanometers and more particularly, to an accessory for application upon conventional blood pressure cuffs to permit the patient to apply same.

With the ever increasing awareness of the implications of the relationship between a patient's blood pressure and his state of health, there has been an ever continuing aim to make it possible for the individual patient to determine his blood pressure without the necessity of seeking the assistance of another person, or of having to make periodic visits to a clinic or doctor's office. The placement of the usual cuff about the patient's limb, such as, normally, the upper arm overlying the brachial artery, has required the utilization of at least two hands, and with the heretofore conventional sphygmomanometer, the positioning of the same has rendered the hand of the arm upon which the cuff is being mounted substantially useless so that the individual patient was helpless to effect his own reading since the cuff could not be manipulated by a single hand.

To overcome this problem there have been numerous efforts to develop blood pressure measuring devices which are specially constructed for one-hand mounting. For instance, in U.S. Pat. No. 3,929,129 there is disclosed a cuff comprising an arm-encircling band utilizing a slide fastener to permit limb encirclement.

In U.S. Pat. No. 3,906,927, the particular cuff is designed to embody a spiral clip which is prestressed and promotes holding of the cuff in position so that the user can effect an appropriate measurement.

U.S. Pat. No. 4,007,734 departs from the conventional indicating device, and includes novel pressure switches, obviating the incorporation of the usual aneroid manometer and, thus, simplifies the determination of the systolic-diastolic pressures without utilization of the services of another individual.

The Raczkowski U.S. Pat. No. 4,033,337 shows another form of sphygmomanometer cuff which may be applied by the individual patient without assistance and incorporates elastic bands for encircling the particular limb when inserted into the cuff loop within which the bands are located.

Thus, such prior efforts have been directed to developing sphygmomanometers which integrally embody expedients for positioning the cuff in order that determination may be made on a self-monitoring basis. Such developments have necessarily been costly by requiring a complete reconstruction, rather than a consideration of means for adapting pre-existing blood pressure cuffs for ease of application by an individual without the necessity of extensively altering the basic construction involved.

Therefore, it is an object of the present invention to provide an accessory for blood pressure cuffs as constituents of sphygmomanometers which may be easily and readily applied thereon without altering the involved operating components.

It is another object of the present invention to provide an accessory of the character stated which, in actuality, may be applied upon the particular cuff by the individual patient so that marked economy is effected.

It is still another object of the present invention to provide an accessory of the character stated which is extremely inexpensive and durable in usage; and which, furthermore, is quite easily manipulated by the patient so that no particular extensive instructional efforts are required.

It is another object of the present invention to provide an accessory of the character stated which does not cause any alteration whatever in the manner of blood pressure measurement by the sphygmomanometer involved so that a patient may continue with the measurement system with which he has become most familiar.

It is a further object of the present invention to provide an accessory of the character stated which assures the patient of complete independence of any other individual in effecting blood pressure measurement and thereby allows of easily effected monitoring programs which are quite often requisite in providing necessary data for the treatment in question.

DESCRIPTION OF THE PREFERRED EMBODIMENT

Figure 1:
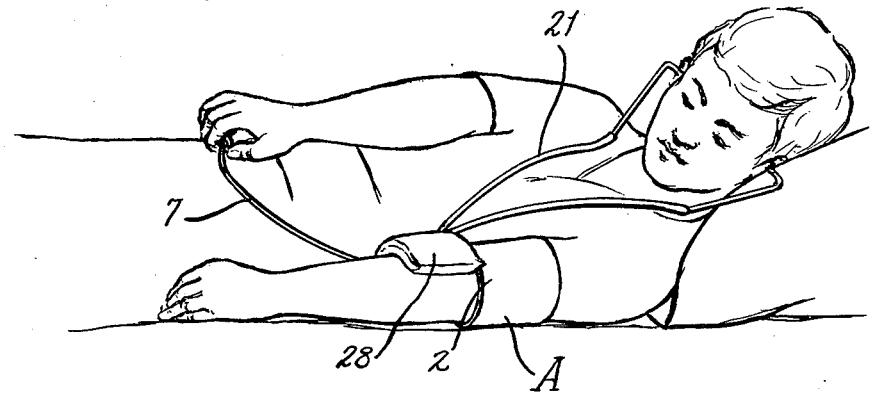
FIG. 1 is a perspective view of a blood pressure cuff mounted on the limb of the user in operating condition, which cuff incorporates a self-applying accessory constructed in accordance with and embodying the present invention.

Referring now to the drawings which illustrate the preferred embodiment of the present invention, A designates a blood pressure indicator, or sphygmomanometer, which is of widely accepted, generally conventional form, incorporating a flexible cuff 1 formed of durable, non-elastic fabric divided into two sections 2,3 which may be formed unitarily or from independent sections joined as by a line of stitching. Each section 2,3 includes two layers of fabric 4,5 which are secured along their side and end margins, as by stitching s. Section 3, between the associated fabric layers 4,5 constitutes a chamber c for receiving the usual inflatable air bladder 6, with there being a flexible tube 7 extending from said bladder through an opening, as at 8, between the layers 4,5 for extension outwardly. Secured upon the end of tube 7 is the usual hand-squeezeable, inflating or pressure bulb 9 having associated therewith the expected bleed valve 10. A second flexible tube 11 is connected to bladder 6 and also passes outwardly through opening 8 with there being mounted on its outer extremity the usual aneroid manometer 12.

Provided for lending a certain desired, limited weightiness and form retention to cuff 1, are stiffening elements, as of plastic, thin metal, or the like located adjacent the outer or free ends of sections 2,3, as at 13, 14, respectively, which are restrained against displacement by lines of stitching 15, 16, respectively, which collaborate with the end edges of cuff 1 to form suitable stiffener chambers. In many of these conventional models, often times a single stiffener is presented at the free end of the section corresponding to section 2. With the present invention there is also provided a substantially central stiffener 17 which is held against lateral displacement by parallel lines of stitching 18,18', the former constituting the inner limit of bladder chamber c. It is to observed that stiffener 17 is of less length than the width of cuff 1 so that at either end there is provided a relatively short fabric portion p.

Provided upon the outer face of fabric layer 4, proximate the free end of section 3, is a cooperative fastener element 19, such as a patch or section of a medium identified by the trademark VELCRO, and constituting a multiplicity of small barbs. A cooperative fastening component 20 is suitably mounted on the outer face of fabric layer 5 on section 2 and is shown as also being of VELCRO, and comprising a multiplicity of small loops for engaging the barbs of member 19, for purposes presently appearing.

Fastener member 20 is preferably of greater longitudinal extent relative to fastener 19 for assuring of appropriate interengagement in accommodating arms of various circumferences.

It will thus be seen that the blood pressure indicator A hereinabove described is of a most common and widely utilized character and no invention is asserted as to the basic or fundamental structure thereof. The foregoing description is thus intended to fully inform as to the environment within which the present invention may be used to highlight its adaptability for use with well known sphygmomanometer types without necessitating any basic alteration in the character and functionality of the components thereof. However, it is to be observed that centrally located stiffener 17 is an element introduced for promoting the effectiveness of the present invention.

It will be appreciated that in utilizing indicator A, cuff 1 is disposed encirclingly about the upper arm of the patient with the fasteners 19,20 being interengaged for retaining the device in operative position so that bladder 6 may be filled to the appropriate extent to occlude blood flow in the brachial artery, with such condition being determined by the customary utilization of the usual stethoscope 21. The air pressure in bladder 6 is then relieved until the Korotkoff tapping sounds are detected, as by the stethoscope 21, with a reading being made from the gage 12' of manometer 12 for determining the systolic blood pressure. The pressure within the cuff is permitted to continue to fall, with the Korotkoff sounds becoming muffled and finally inaudible, at which point the gage reading indicates the diastolic blood pressure.

It will, accordingly, be seen that without assistance an individual would be unable to apply cuff 1 since the requisite procedure of such application and of operating the device cannot be accomplished by the use of the single available hand.

Figure 2:
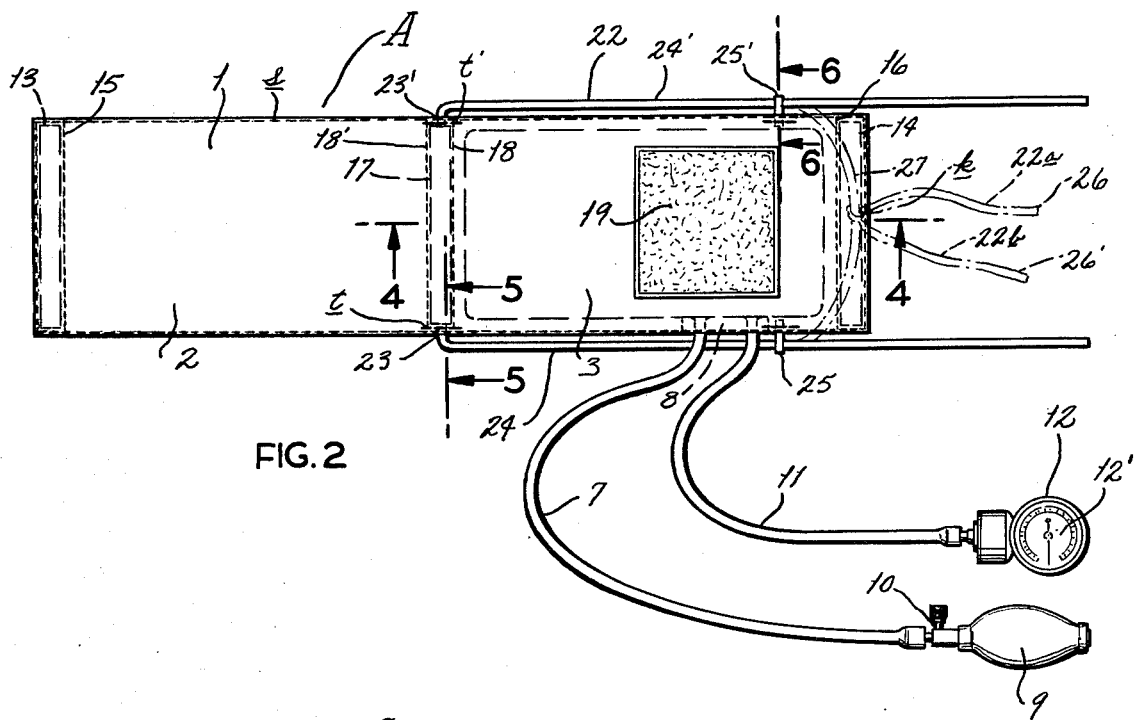
FIG. 2 is a front plan view of the blood pressure indicator or sphygmomanometer.
Figure 3:
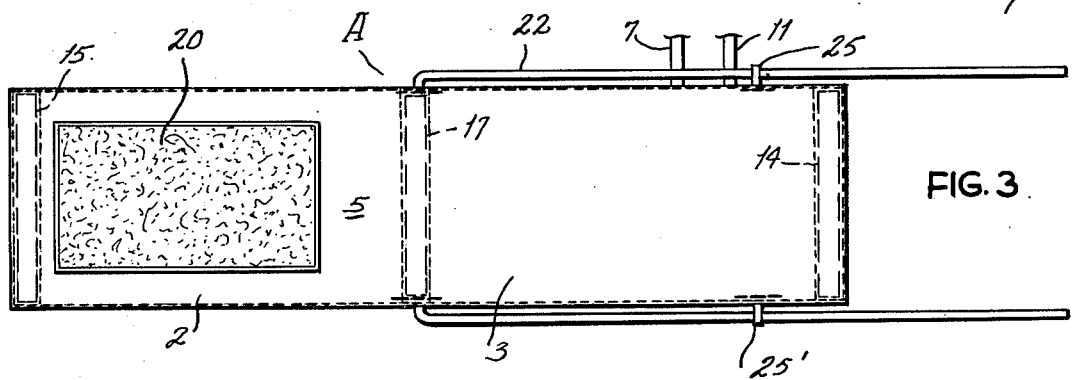
FIG. 3 is a rear plan view.
Figure 4:
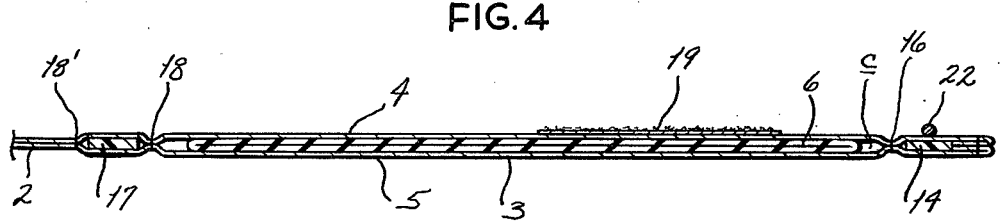
FIG. 4 is a vertical transverse sectional view taken on the line 4—4 of FIG. 2.
Figure 5:
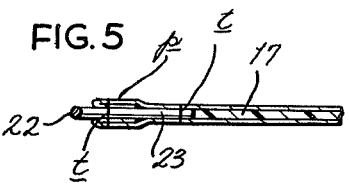
FIG. 5 is a vertical transverse sectional view taken on the line 5—5 of FIG. 2.
Figure 6:
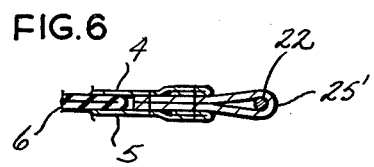
FIG. 6 is a vertical transverse sectional view taken on the line 6—6 of FIG. 2.

With reference now being made to FIG. 2, a non-elastic control cord 22 is provided for facilitating encirclement of the patient's arm by cuff 1 and, although it may be constituted of a single integral length, is preferably formed of a pair of components 22a and 22b each having a normally free inner end 23, 23', which latter are secured, as by stitching t,t', to the fabric layers 4,5 in the respective portions p thereof (FIGS. 2 and 5). Each cord component 22a, 22b contains an intermediate section 24, 24', respectively, in opposed relationship which progress from each end 23, 23', respectively, in substantially parallel relation to the adjacent edge cuff section 3, when indicator A is in extended, non-use state (FIG. 2); with intermediate sections 24, 24' passing freely through eyelets 25,25', respectively, fixed to the adjacent edge of section 3 spacedly from, but adjacent the proximate end extremity of said section 3. Beyond eyelets 25, 25' said opposed sections 24,24' terminate in outer free end portions 26,26', respectively, for interengagement, as by a suitable tie or knot k to thereby complete a general loop formation to cord 22. Cord 22 is, accordingly, retained to cuff section 3 at the free ends 23,23' thereof and with eyelets 25,25' serving to guide said cord within the prescribed path for cooperating with cuff section 3 for purposes now to be described.

With cuff 1 in extended condition, as shown in FIG. 2, lifting upwardly upon united cord end section, as indicated generally at 27, will cause cord sections 24,24' to move relatively through eyelets 25,25' as cuff section 3 is commensurately raised and brought into a general loop-forming relationship to the zone of cuff 1 intermediate sections 2,3 thereof as substantially defined by stiffener 17 which thus serves as an anchor. Thus, cord 22 does act to control the movement of cuff section 3 without direct manipulation of such section.

Figure 7:
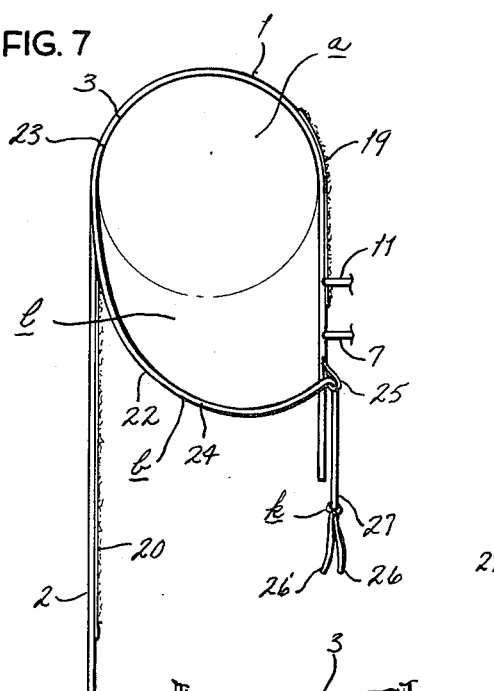
FIGS. 7, 8 and 10 are end views which sequentially show the disposition of the accessory during the operation thereof for applying the cuff about the user's limb.
Figure 9:
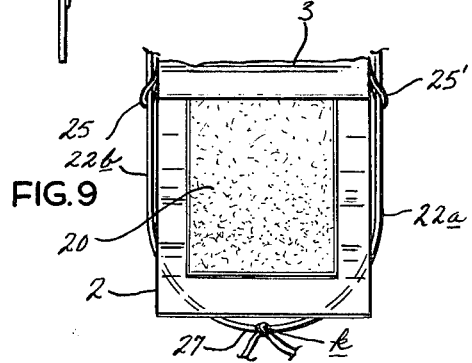
FIG. 9 is a fragmentary view taken on the line 9—9 of FIG. 8.
Figure 8:
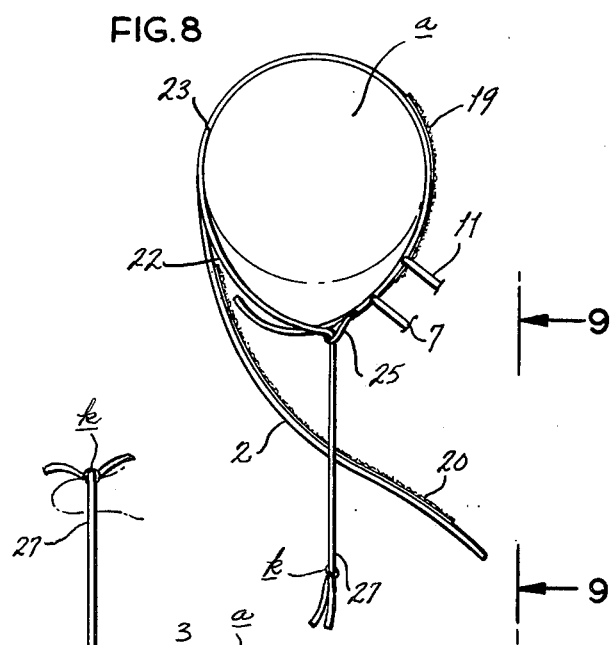
Figure 10:
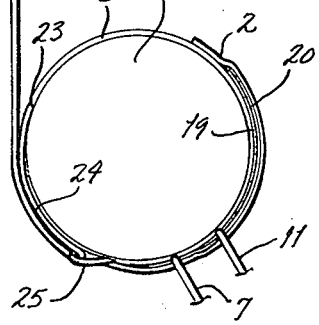

Reference is now made to FIGS. 7, 8 and 10 which endeavor to illustrate sequentially the function of cord 22 in positioning cuff 1 and in which FIGURES a signifies the upper arm of the patient. In order to dispose section 3 upon arm a, the same is caused to be generally arched for ultimate conformance to the curvature of the arm and by such movement the intervening distance between the secured free ends 23,23' and the proximate eyelets 25,25' is understandably reduced so that the intervening portions of cord sections 24,24' are relatively lengthened and thus will hang downwardly, as at b, and cooperate with the now curved, or arched, section 3 to form enlarged aligned loops, as at 1, through which the user will extend arm a. As so extended, arm a will support section 3 which is disposed drapingly thereon, with fastener section 19 being directed laterally outwardly, and with tubes 7,11 extending outwardly. It will be seen that cord end section 27 will also be in depending condition projecting below the free end edge of section 3. Section 2 of cuff 1 will thus hang downwardly from the inner side of arm a, with the cooperating fastener section 20 being directed laterally outwardly.

The user will then grasp the depending cord section 27 with the hand of the opposite arm and pull downwardly (see FIG. 8), which draws the portions of the loops l snugly about arm a, as the major portions of cord 24,24' move downwardly through the respective eyelets 25,25'. Such action will cause end section 27 to form an enlarged loop through which the user will project cuff section 2 (see FIG. 8). When section 3 with the now tightened cord 24 is snugly about arm a, the user will then release end section 27 from the grasp of the hand of the opposite arm, that is, the one upon which measurement is not being taken, and grasp or engage the extremity of end section 27, as by the thumb of the hand of the arm upon which the measurement is being taken, and thereby freeing the other hand. The user will lift the cord upwardly to place maximum tension thereon so as to assure of snug gripping of arm a by section 3 and the now spatially reduced portion of sections 24,24', and then simply grasp section 2 and move it outwardly and upwardly about section 3 so as to bring fastener section 20 into engagement with cooperative fastener portion 19 and thereby render cuff 1 in proper operating condition. Thereupon, the user may release cord section 27 with assurance that cuff 1 is reliably secured. The user's hands are then both free for appropriate manipulation of the operative components so that an accurate blood pressure reading may be effected. The user having located the appropriate zone on the cuff-encircled arm for pulse detection will place the receptor (not shown) of stethoscope 21 thereupon and then place a weighted item, such as a pad 28 containing relatively heavy material of any desired type upon said receptor to prevent its displacement during the measuring operation. Said pad 28 may very well resemble, among others, the conventional bean bag. With the receptor so stabilized, the user may then grasp pressure bulb 9 with the hand of the arm free of cuff 1, as in this case the right hand, and can readily effect the necessary compression and relaxation to assure of accurate indication on manometer 12, which may be held in the opposite hand, that is, of the arm bearing cuff 1 so that the systolic and diastolic pressures can be accurately determined. After the blood pressure determination has been effected, the user will break the engagement between fastener sections 19,20 in the usual manner, that is, by appropriately lifting section 2 so as to return the same to depending position. Cord sections 24, 24' are pulled downwardly to restore loops 1 so as to allow easy withdrawal of the arm through the opening developed thereby.

Thus, from the foregoing, it is readily observed that cord 22 is a most simple, yet highly efficacious, accessory for a conventional blood pressure cuff to permit a patient to properly and reliably dispose such cuff in position for proper usage entirely independent of the services of another individual. It is clear that cord 22, together with eyelets 25, 25' may be simply affixed to an existing fabric cuff so that modification of the cuff in either basic construction, or component substitution, is obviated. Furthermore, the application of cord 22 for assuring of disposition of the cuff is a simple procedure which can be easily achieved by the average individual and thus permit the same to monitor blood pressure without the intervention of the services of another party.

It will be seen that stiffener 17 does promote positioning of cuff section 3, as well as provide a suitable anchor for cord 22 during cuff-mounting and cuff-dismounting manipulation and movement thereof.

From the foregoing it is, of course, apparent that cord 22 may be of a unitary length, but to render cuff 1 more versatile in usage it has been found desirable that said cord actually be constituted of two independent components which may be tied or otherwise united proximate their outer free ends so that the resulting loop formation will be of a magnitude compatible with the size of the user's arm and thus assure appropriate, stabilized encirclement of cuff 1 without regard to how thick the user's arm may be.

What is claimed is:

1. In a blood pressure cuff comprising first and second flexible section having opposed side edges, inner end portions, and outer free ends, means securing said cuff sections at their inner end portions in end to end relationship for disposition between a coplanar extended inoperative condition and overlapping, encircling disposition about a patient's arm, first and second cooperative fastener components provided respectively upon said first and second cuff sections for interengagement for maintaining said cuff in operative disposition, the improvement comprising an accessory for facilitating operative disposition of the cuff by the user, said accessory comprising an elongated member of flexible material having first and second lengths having outer free ends normally proximate the outer free end of said cuff second section, said first and second lengths of said elongated member having inner end portions, means fixedly securing the inner end portions of said first and second lengths of said elongated member in the region of securement of the inner end portions of said cuff first and second sections, said elongated member first and second lengths each having central portions between the respective fixed inner end portions and outer free ends thereof located adjacent the side edges of said cuff second section when said cuff is in an inoperative state, the outer free ends of the first and second lengths of the elongated member being mutually secured proximate the free end of said cuff second section, and guide means provided on said cuff second section for the adjacent central portions of said first and second lengths of the elongated member, said guide means being located between the inner end portion and outer free end of said second cuff section for permitting relative movement between said second section and said elongated member during disposition of the cuff into operative position.

2. The improvement as defined in claim 1 wherein said elongated member of flexible material is of cord, and said guide means are eyelets secured upon the related side edges of said second cuff section, and being of greater cross section than said cord so as to permit free movement of the cord through the eyelets.

3. The improvement as defined in claim 2 wherein said first and second flexible sections of said cuff are constructed of fabric, said means securing said first and second sections of fabric, said means securing said first and second sections of said cuff at their inner end portions being by way of stitching.

4. The improvement as defined in claim 3 wherein stiffener means are provided within said cuff in the region of the securement of the inner end portions of said elongated member.

5. The improvement as defined in claim 3 wherein stiffener means are provided within said cuff within the region of securement of the inner end portions of said first and second sections of said cuff and between the means fixedly securing the inner end portions of the elongated member to said cuff.

6. The improvement as defined in claim 2 wherein the eyelets are so located relative to the secured outer free ends of said first and second lengths of the elongated member so that the central portions of said first and second lengths will cooperate to form a loop when said second cuff section is in operative dispostion.

* * * * *

UNITED STATES PATENT AND TRADEMARK OFFICE
CERTIFICATE OF CORRECTION

PATENT NO. : 4,465,076

DATED : August 14, 1984

INVENTOR(S) : Sturgeon

It is certified that error appears in the above-identified patent and that said Letters Patent is hereby corrected as shown below:

Column 6, claim 3, lines 44 and 45, delete "said means securing said first and second sections of fabric,".

Signed and Sealed this

Fifteenth Day of January 1985

[SEAL]

Attest:

GERALD J. MOSSINGHOFF

Attesting Officer

Commissioner of Patents and Trademarks